United States Patent [19]
> Burckhardt et al.

[11] 4,101,585
[45] Jul. 18, 1978

[54] PROCESS FOR THE PRODUCTION OF DEOXY-ALPHA-ACIDS

[75] Inventors: Urs Burckhardt, Basel; Lucius Werthemann, Riehen; Richard Josef Troxler, Birsfelden, all of Switzerland

[73] Assignee: Ciba-Geigy Corporation, Ardsley, N.Y.

[21] Appl. No.: 718,710

[22] Filed: Aug. 30, 1976

[51] Int. Cl.$^2$ ............................................. C07C 49/82
[52] U.S. Cl. .................................................... 260/592
[58] Field of Search ..................... 260/592, 591, 624 B, 260/624 C, 624 R

[56] References Cited

U.S. PATENT DOCUMENTS

| | | | |
|---|---|---|---|
| 3,605,760 | 9/1971 | Kallianos et al. | 131/17 R |
| 3,846,498 | 11/1974 | Wild et al. | 260/592 |
| 3,983,175 | 9/1976 | Tamai et al. | 260/592 |
| 3,984,475 | 10/1976 | Tamai et al. | 260/592 |

FOREIGN PATENT DOCUMENTS

| | | | |
|---|---|---|---|
| 1,227,144 | 3/1968 | United Kingdom | 260/465 |
| 1,167,679 | 7/1968 | United Kingdom | 260/591 |

OTHER PUBLICATIONS

Brandstrom et al., Tetrahedron Letters, 1972 (6), pp. 473-474.
Durst et al., J. Org. Chem., vol. 39(22), pp. 3271-3272 (1974).

Primary Examiner—James O. Thoms, Jr.
Assistant Examiner—James H. Reamer
Attorney, Agent, or Firm—Karl F. Jorda

[57] ABSTRACT

Preparation of deoxy-α-acids (deoxyhumulons) by prenylation of the corresponding acylphloroglucinols under alkaline conditions, whereby prenylation is performed in a mixture of water and an organic solvent immiscible with water, in the presence of a phase-transfer catalyst.

8 Claims, No Drawings

PROCESS FOR THE PRODUCTION OF DEOXY-ALPHA-ACIDS

The present invention relates to a process for the production of deoxy-α-acids by prenylation of acylphloroglucinols.

The deoxy-α-acids (deoxyhumulons) obtainable according to the invention correspond to formula I

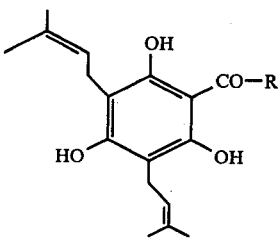

wherein
R represents a straight-chain or branched-chain alkyl group having 1 to 5 carbon atoms.

These compounds can be converted by oxidation into α-acids (humulons), which are identical to the bitter principles present in hop resin. The α-acids convert then in the brewing process into iso-α-acids, which are responsible for the specific bitter taste of the beer.

Various processes have hitherto become known for obtaining the deoxy-α-acids, required as starting material for the production of synthetic bitter principles, by prenylation of acylphloroglucinols. Thus, for example, acylphloroglucinols were reacted in methanol in the presence of sodium methylate, or in water in the presence of potassium hydroxide, with prenyl bromide to give deoxy-α-acids (see W. Riedel et al., Chem. Ber. 90, 2870–2876 (1957)). By this process is obtained however merely a yield of 10 to 15% of the desired deoxy-α-acids. Such yields are too low for carrying out the process commercially. According to a further process, described in the British Patent Specification No. 1,355,236, deoxy-α-acids are produced by reaction of acylphloroglucinol with α,α-dimethylallyl alcohol in the presence of boron trifluoride. The yield of less than 28% obtained also by this process is very low. Another process, described in the German Offenlegungsschrift No. 2,333,580, comprises reacting acylphloroglucinols with prenyl chloride in acetone in the presence of magnesium oxide and potassium iodide. The gross yield of about 55 to 75% obtained by this process is acceptable. The resulting products are however so impure that the gross yield decreases to a net yield of about 40 to 45%. In the embodiments of this process, which are illustrated by examples, prenylation is performed in acetone as solvent at the reflux temperature of the reaction mixture with a reaction time of 11 to 16 hours. These long reaction times in conjunction with the relatively high reaction temperatures have to be considered disadvantageous in view of the low stability of the final products.

It has now been found that the deoxy-α-acids of formula I can be obtained in good yields by reaction of acylphloroglucinols of formula II

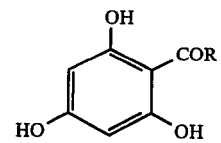

wherein
R represents a straight-chain or branched-chain alkyl group having 1 to 5 carbon atoms, under alkaline conditions with a prenyl halide, whereby prenylation is performed in a mixture of water and an organic solvent immiscible with water, in the presence of a phase-transfer catalyst.

Suitable organic solvents immiscible with water are: hexane, benzene, toluene, xylene, chlorobenzene, chloroform, methylene chloride, ethylene chloride and diethyl ether. Preferred solvents are hexane, toluene, chloroform and methylene chloride, and especially chlorobenzene.

Phase-transfer catalysts are in general: tetraalkylammonium salts and tetraalkylphosphonium salts, e.g. halides and sulfates, such as methyltrioctylammonium chloride, trimethylbenzylammonium chloride, tetrabutylammonium bisulfate, dimethylbenzylhexadecylammonium chloride, tetraethylammonium chloride and tetrabutylphosphonium bromide.

Also suitable are crown ethers, e.g. 1,4,7,10,13,16-hexaoxacyclooctadecane (18-crown-6). Preferred phase-transfer catalysts are methyltrioctylammonium chloride, trimethylbenzylammonium chloride and tetrabutylammonium bisulfate.

The phase-transfer catalysts are added to the reaction mixture in amounts of 0.01 – 0.1 mole, preferably 0.03 to 0.06 mole, per mole of acylphloroglucinol.

The reaction temperatures are according to the invention between −10° and +40° C, preferably between −5° C and +5° C. The reaction times are between 15 minutes and 5 hours, preferably 2 hours.

Basic reaction conditions are obtained by adding to the reaction mixture alkali metal hydroxides, such as lithium hydroxide, sodium hydroxide and, in particular, potassium hydroxide. Prenylation is preferably performed at a pH-value between 10.5 and 12.5, whereby the optimum pH-value depends on the radical R of the acylphloroglucinols of formula II. After completed reaction, the reaction mixture contains, in addition to the desired deoxy-α-acids of formula I and unreacted starting material, as by-products in particular geminally alkylated products of the following formulae III and IV.

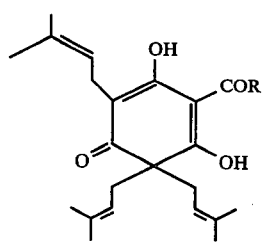

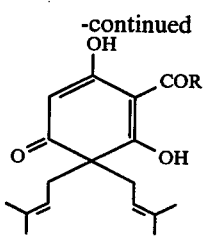

These products present in the reaction mixture can be readily separated by virtue of their differing alkali solubility. Separation can be effected by extraction of the reaction mixture with diethyl ether at varying pH-value. For this purpose, the pH-value of the reaction mixture is adjusted firstly to 14 by the addition of alkali metal hydroxide and the by-products of formula III are extracted, together with chromans formed from these by ring closure, and also 0-alkylation products, organic solvents and the quaternary ammonium hydroxides formed from the employed phase-transfer catalysts. There is subsequently separated at a pH-value between 11.0 and 12.5 the desired deoxy-α-acid, whereby the optimum pH-value depends on the radical R of the deoxy-α-acid of formula I. From the mother liquor can then be separated, by extraction at a pH-value of between 8.5 and 10, the geminal alkylation products of formula IV, and by extraction at a pH-value of about 5 the unreacted starting material.

The acylphloroglucinols of formula II used as starting material can be produced by reaction of phloroglucinol with acyl halides in the presence of aluminum chloride and nitrobenzene in methylene chloride (see W. Riedel, Liebigs Ann. Chem. 585, 38, (1954)).

Although the prenylation of acylphloroglucinols according to the invention is performed at low temperatures, reaction times shorter than those in the case of known processes are required. At the same time, the net yield of deoxy-α-acids is increased to 50 to 55% of theory.

Deoxy-co-α-acid (R = isopropyl), deoxy-n-α-acid (R = isobutyl), deoxy-ad-α-acid (R = sec.butyl), deoxy-pre-α-acid (R = isoamyl) and deoxy-post-α-acid (R = ethyl) can be produced by the process according to the invention.

These deoxy-α-acids can be converted in a known manner by oxidation into the corresponding α-acids (humulons), from which are then formed iso-α-acids by isomerisation, which are known as bitter principles and which can be used, for example, for rendering the beer more bitter (see J. Wild et al., 'Schweizerische Brauerei-rundschau' (Swiss Brewing Review) 87 (½), 59–63, (1976) and German Offenlegungsschrift 2,333,580). The process according to the invention is further illustrated by the following Examples.

EXAMPLE 1

3,5-bis-[γ,γ-dimethylallyl]-phloroisovalerophenone

A mixture of 8.4 g (0.04 mole) of phloroisovalerophenone, 40 ml (0.08 mole) of 2N potassium hydroxide solution, 70 ml of chlorobenzene and 0.81 g (0.002 mole) of Aliquat 336 (methyltrioctylammonium chloride) is placed under nitrogen in a 350 ml flask provided with stirrer, thermometer, pH-electrode and 2 dropping funnels; the mixture is cooled to 0° C and its pH value is adjusted to 12 by the addition of 2N hydrochloric acid. An addition is then made dropwise, with a stirring rate of 2000 r.p.m. at 0° C, of 12.0 g (0.08 mole) of 1-bromo-3-methylbut-2-ene (prenyl bromide), whereby the pH-value is maintained at 12 by the addition of potassium hydroxide solution. After completion of the addition, stirring is continued for 4 hours at 0° C. The pH-value is subsequently brought to 14 by the addition of potassium hydroxide solution; the chlorobenzene is separated and the aqueous phase is extracted three times with 150 ml of ether each time, and the extracts are combined with the chlorobenzene phase. The oily residue (fraction 1) obtained after drying with sodium sulphate and removal of the solvent by evaporation is discarded.

The alkaline aqueous solution is thereupon covered over with 50 ml of ether and, with vigorous stirring, the pH-value is adjusted to 12 by the addition of concentrated aqueous hydrochloric acid. After separation of the ether layer, the aqueous phase is extracted again three times with 150 ml of ether each time. The combined extracts are dried with sodium sulfate, and the ether is evaporated off in vacuo at 40° C to leave as residue 7.6 g (54.8% of theory) of 3,5-bis-[γ,γ]-dimethylallyl-phloroisovalerophenone (deoxy-n-α-acid) (fraction II).

The aqueous phase is subsequently covered with 50 ml of ether and, with vigorous stirring, the pH-value is brought to 9.5 by the addition of concentrated hydrochloric acid. After separation of the ether phase, extraction is performed a further three times with 150 ml of ether each time. The combined ether phases are dried with sodium sulfate, and the ether is evaporated off in vacuo. There is obtained 1.5 g (10.85% of theory) of the geminal compound of formula IV (R = isobutyl) in the form of red oil (fraction III).

The aqueous phase remaining is subsequently acidified with concentrated hydrochloric acid and extracted three times with 150 ml of ether each time. The combined ether extracts are dried with sodium sulfate and the ether is evaporated off in vacuo to obtain 1.8 g (21% of theory) of phloroisovalerophenone as crude oil (fraction IV).

The phloroisovalerophenone used as starting material is produced as follows:

Into a stirred suspension of 125 g (1.0 mole) of phloroglucinol in 1 liter of methylene chloride is firstly introduced 400 g (3.0 moles) of aluminium chloride, and immediately afterwards an addition is made dropwise, in the course of ½ hour, of 370 ml of nitrobenzene, whereby, with an intense evolution of hydrogen chloride and an increase of temperature to 30° to 35° C, the reaction mixture becomes homogeneous. A solution of 125 g (1.0 mole) of isovaleroyl chloride in 30 ml of nitrobenzene is subsequently added dropwise at 35° to 40° C during ½ hour. After completion of the addition, stirring is maintained at 35° C for one hour; the reaction mixture is allowed to cool to 30° C and is then poured onto a mixture of 2 kg of ice and 200 ml of concentrated hydrochloric acid. From the resulting mixture, methylene chloride is firstly distilled off in vacuo, and subsequently the nitrobenzene is expelled with steam. From the aqueous phase remaining behind, there firstly precipitates crude phloroisovalerophenone as a dark oil which solidifies below 90° C. On cooling to 10° C, a further fraction of phloroisovalerophenone crystallises out in the form of yellow flakes. The crude phloroisovalerophenone is filtered off under suction and dissolved in 1 liter of ether. The ethereal solution is dried with sodium sulfate, filtered through 200 g of silica gel 60 and subsequently rinsed with 1 liter of ether. The ether is evaporated off to leave 184 g (88.5% of theory) of crude phloroisovalerophenone with a melting point of 138°–140° C.

To purify the crude product, it is dissolved in 100 ml of hot ethyl acetate and, after the addition of 9.0 g of active charcoal, the solution is stirred under reflux for half an hour. It is afterwards filtered hot and then washed with 30 ml of hot ethyl acetate. One liter of methylene chloride is added to the filtrate and the temperature is lowered to 0° C, whereupon the pure chloroisovalerophenone precipitates. Yield: 150 g (71% of theory); m.p. 142° – 143.5° C.

Acylphloroglucinols of formula II having different radicals R can be produced in an analogous manner.

EXAMPLE 2

In a manner analogous to that described in Example 1, various acylphloroglucinols of formula II were prenylated. The results are summarised in the following Table, wherein the yields for the individual fractions are given in % of theory. The number in brackets after the yield value indicates the pH-value at which the respective fraction was separated. Purification of the crude deoxy-α-acids (fraction II) was effected by recrystallisation from hexane or, in cases where the occurring deoxy-α-acids of formula I are oils, by boiling with pentane and separation of the constituents insoluble in pentane.

EXAMPLE 3

The production of 3,5-bis-[γ,γ-dimethylallyl]-phloroisovalerophenone was repeated with the amounts of starting materials and the reaction conditions being kept as given in Example 1.

The crude deoxy-n-α-acid (3,5-bis-[γ,γ-dimethylallyl]-phloroisovalerophenone), obtained by extraction with ether at pH 12, drying of the extract with sodium sulfate and removal of the ether by evaporation in vacuo at a maximum of 40° C, is purified in a column with the use of 350 g of silica gel and ether/petroleum ether (5 : 6) as the eluant. From 7.8 g (56.3% of theory) of crude deoxy-n-α-acid, m.p. 67° C, are obtained 7.3 g (52.6% of theory) of pure deoxy-n-α-acid, m.p. 71° – 73° C.

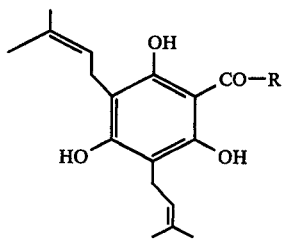

wherein
R represents a straight-chain or branched-chain alkyl group having 1 to 5 carbon atoms, by prenylation of acylphloroglucinols of formula II

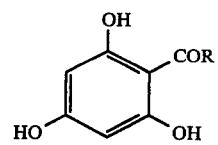

wherein R has the meaning given under formula I, under alkaline conditions with a prenyl halide, in which process prenylation is performed in a mixture of water and an organic solvent immiscible with water, in the presence of a phase-transfer catalyst selected from the group consisting of tetraalkylammonium salts, tetraalkylphosphonium salts and crown ethers.

2. Process according to claim 1, wherein the employed solvent immiscible with water is hexane, benzene, toluene, xylene, chlorobenzene, chloroform, methylene chloride, ethylene chloride or diethyl ether.

3. Process according to claim 1, wherein the employed solvent immiscible with water is chlorobenzene.

4. Process according to claim 1, wherein the phase-transfer catalyst used is methyltrioctylammonium chloride, trimethylbenzylammonium chloride, tetrabutylammonium bisulfate, dimethylbenzylhexadecylammonium chloride, tetraethylammonium chloride or tetrabutylphosphonium bromide.

5. Process according to claim 1, wherein the phase-transfer catalyst used is methyltrioctylammonium chlo-

| R | pH-value on prenylation | Fraction I (pH) | Fraction II (pH) crude | Fraction II pure | m.p. | Fraction III (pH) |
|---|---|---|---|---|---|---|
| $CH_3$ | 10.5 | 10 (14) | 58 (11,3) | | 75–77° C | 21 (8,5) |
| $C_2H_5$ | 11,0 | 14 (14) | 56 (11,0) | 45 | oil | 29 (8,5) |
| $C_3H_7$ (iso) | 11,3–11,5 | 12 (14) | 57 (11,5) | 50 | 88–90° C | 24 (9,0) |
| $C_4H_9$ (sec.) | 11,5 | 7,2 (14) | 57 (12,0) | 51 | oil | 22 (9,5) |
| $C_5H_{11}$ (iso) | 12,5 | 15,7 (14) | 55 (12,5) | 50 | 68–69,5° C | 20 (10) | ride, trimethylbenzylammonium chloride or tetrabutylammonium bisulfate.

6. Process according to claim 1, wherein the phase-transfer catalyst is used in amounts of 0.01 to 0.1 mole, preferably 0.03 to 0.06 mole, per mole of acylphloroglucinol of formula II.

7. Process according to claim 1, wherein pyrenylation is performed at temperatures between −10° and +40° C.

8. Process according to claim 1, wherein prenylation is performed at temperatures between −5° C and +5° C.

We claim:
1. Process for the production of deoxy-α-acids of formula I